(12) United States Patent
Stevenson

(10) Patent No.: US 11,253,378 B2
(45) Date of Patent: Feb. 22, 2022

(54) HANDS-FREE APPARATUS TO APPLY A LINER TO AN AMPUTATED APPENDAGE

(71) Applicant: Tim Lee Stevenson, Galt, CA (US)

(72) Inventor: Tim Lee Stevenson, Galt, CA (US)

( * ) Notice: Subject to any disclaimer, the term of this patent is extended or adjusted under 35 U.S.C. 154(b) by 51 days.

(21) Appl. No.: 15/929,494

(22) Filed: May 5, 2020

(65) Prior Publication Data

US 2020/0368043 A1 Nov. 26, 2020

Related U.S. Application Data

(60) Provisional application No. 62/852,505, filed on May 24, 2019.

(51) Int. Cl.
*A61F 2/78* (2006.01)
*A47G 25/90* (2006.01)
*A61F 2/50* (2006.01)

(52) U.S. Cl.
CPC .......... *A61F 2/7812* (2013.01); *A47G 25/905* (2013.01); *A61F 2002/507* (2013.01); *A61F 2002/5069* (2013.01); *A61F 2002/7825* (2013.01); *A61F 2002/7837* (2013.01); *A61F 2002/7868* (2013.01)

(58) Field of Classification Search
CPC .................. A47G 25/905; A61F 2/7812; A61F 2002/7825; A61F 2002/7837; A61F 2002/7868; A61F 2002/5069; A61F 2002/507
See application file for complete search history.

(56) References Cited

U.S. PATENT DOCUMENTS

| | | | |
|---|---|---|---|
| 2,666,927 A | 1/1954 | Morheiser | |
| 2,834,025 A | 5/1958 | Leavy | |
| 3,601,819 A | 8/1971 | Herrmann | |
| 3,922,727 A | 12/1975 | Bianco | |
| 4,038,701 A | 8/1977 | McFall et al. | |
| 5,203,791 A | 4/1993 | Blanchard | |
| 5,326,351 A | 7/1994 | Sarazin | |
| 5,658,353 A | 8/1997 | Layton | |
| 5,800,572 A | 9/1998 | Loveall | |
| 6,334,876 B1 | 1/2002 | Perkins | |
| 6,536,636 B1 * | 3/2003 | McDonniel | A47G 25/905 223/111 |
| 6,793,682 B1 | 9/2004 | Mantelmacher | |
| 7,662,191 B2 | 2/2010 | Asgeirsson | |
| 7,883,547 B2 | 2/2011 | Mantelmacher | |
| 8,080,065 B2 | 12/2011 | Scussel et al. | |
| 8,113,235 B2 | 2/2012 | Bogue | |

(Continued)

*Primary Examiner* — Javier G Blanco
(74) *Attorney, Agent, or Firm* — Innovation Capital Law Group, LLP; Vic Lin

(57) ABSTRACT

A liner to an appendage of a user includes a base member, a bracket adjustably mounted to the base member to a desired height position, and a plurality of arms pivotably mounted to the bracket. Each arm can include a rotating member, such as a roller ball, coupled to a top end of the arm. The plurality of arms can extend from the bracket in a generally upright position and can support the liner thereon in an inside out position so that the application of downward pressure by the appendage of the user within the plurality of arms permits the arms to pivot outward, thereby allowing the plurality of arms and roller balls to slide the liner around the appendage of the user.

8 Claims, 10 Drawing Sheets

(56) References Cited

U.S. PATENT DOCUMENTS

| | | | |
|---|---|---|---|
| 8,308,816 B2 | 11/2012 | Slemker et al. | |
| 8,409,298 B2 | 4/2013 | Perkins et al. | |
| 8,641,779 B1 | 2/2014 | Hollard | |
| 8,784,502 B2 | 7/2014 | Macomber et al. | |
| 8,795,386 B2 | 8/2014 | Pianykh et al. | |
| 8,978,224 B2* | 3/2015 | Hurley | A61F 2/80 29/407.1 |
| 9,050,202 B2* | 6/2015 | Bache | A61F 2/80 |
| 9,615,944 B2 | 4/2017 | Will et al. | |
| 9,615,946 B2 | 4/2017 | Halldorsson et al. | |
| 9,737,420 B2 | 8/2017 | Watt et al. | |
| 9,757,256 B2 | 9/2017 | Sandahl | |
| 9,801,736 B2 | 10/2017 | Horton et al. | |
| 9,820,873 B2 | 11/2017 | Sandahl | |
| 10,028,845 B2 | 7/2018 | Jonasson et al. | |
| 10,226,364 B2 | 3/2019 | Radspieler | |
| 2005/0087573 A1* | 4/2005 | Unsworth | A61B 42/00 223/112 |
| 2008/0147202 A1 | 6/2008 | Danzig et al. | |
| 2009/0120975 A1* | 5/2009 | Schoepe | A47G 25/905 223/111 |
| 2013/0211544 A1 | 8/2013 | Jonsson et al. | |
| 2013/0218296 A1 | 8/2013 | Koniuk et al. | |
| 2014/0207253 A1* | 7/2014 | Horton | A61F 2/76 623/33 |
| 2015/0289999 A1 | 10/2015 | Radspieler | |
| 2016/0000583 A1 | 1/2016 | Ballas et al. | |
| 2016/0338859 A1 | 11/2016 | Sverrisson et al. | |
| 2016/0346100 A1 | 12/2016 | Sverrisson et al. | |

* cited by examiner

HANDS-FREE APPARATUS TO APPLY A LINER TO AN AMPUTATED APPENDAGE

CROSS-REFERENCE TO RELATED APPLICATIONS

This application claims the benefit of priority of U.S. provisional patent application No. 62/852,505, filed May 24, 2019, the contents of which are herein incorporated by reference.

BACKGROUND OF THE INVENTION

1. Field of the Invention

Embodiments of the invention relate generally to the use of liners on amputated appendages. More specifically, embodiments of the invention are directed to apparatus to assist in the application of a liner to an amputated appendage.

2. Description of Prior Art and Related Information

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Amputees begin their day by placing a liner or sleeve on their amputated appendage before attaching a prosthetic leg or other member thereon. It is a difficult and frustrating process for the amputee to place the liner on his/her amputated appendage without the use of a hand or appendage, or the assistance of another individual.

As such, there is a need in the industry for a hands-free apparatus that addresses the limitations of conventional processes and devices, which allows an amputee to easily and efficiently apply a liner to his/her amputated appendage without the assistance of others.

SUMMARY OF THE INVENTION

In certain embodiments, an apparatus for use to apply a liner to an appendage of a user is provided. The apparatus can include a base member, a bracket adjustably mounted to the base member to a desired height position, and a plurality of arms pivotably mounted to the bracket, each arm in the plurality of arms comprising a roller ball coupled to a top end of the arm, wherein the plurality of arms, in a generally upright position, is configured to support the liner thereon in an inside out position so that the application of downward pressure by the appendage of the user within the plurality of arms permits the plurality of arms to pivot outward, thereby allowing the plurality of arms and roller balls to slide the liner around the appendage of the user.

In certain embodiments, the roller ball may be replaced with an oscillating member providing oscillating contact points coupled to a top end of each arm.

Embodiments of the present invention provide an apparatus for applying a liner to an appendage of a user comprising a base member; a bracket mounted to a top side of the base member; a plurality of arms, each having a lower end pivotably mounted to the bracket and an upper end having a rotating member attached thereto; an opening formed from the upper end of each of the plurality of arms; and an arm securing member configured to retain the plurality of arms in an upright position.

Embodiments of the present invention further provide a apparatus for applying a liner to an appendage of a user comprising a base member; an extension extending from a top side of the base; a bracket mounted at the top side of the base member to the extension; a pad disposed on and extending upward from a top side of the bracket; a plurality of arms, each having a lower end pivotably mounted to the bracket and an upper end having a rotatable ball attached thereto; an opening formed from the upper end of each of the plurality of arms; and an elastic band configured to retain the plurality of arms in an upright position and further permitting the plurality of arms to resiliently move, causing the opening to expand in size when the user inserts their appendage into the opening.

Embodiments of the present invention also provide a method for applying a liner onto an appendage of a user comprising applying the liner, inside-out, over an opening and down sides of an apparatus, the apparatus comprising a base member, a bracket mounted to a top side of the base member, a plurality of arms, each having a lower end pivotably mounted to the bracket and an upper end having a rotating member attached thereto, the opening formed from the upper end of each of the plurality of arms, and an arm securing member configured to retain the plurality of arms in an upright position; lowering the appendage onto the liner at the opening covered by the liner, causing the arms to resiliently deform outward; and sliding the appendage into an interior of the apparatus, causing the liner to slide along the rotating members and be applied to the appendage of the user.

These and other features, aspects and advantages of the present invention will become better understood with reference to the following drawings, description and claims.

BRIEF DESCRIPTION OF THE DRAWINGS

Some embodiments of the present invention are illustrated as an example and are not limited by the figures of the accompanying drawings, in which like references may indicate similar elements.

Figure 1:
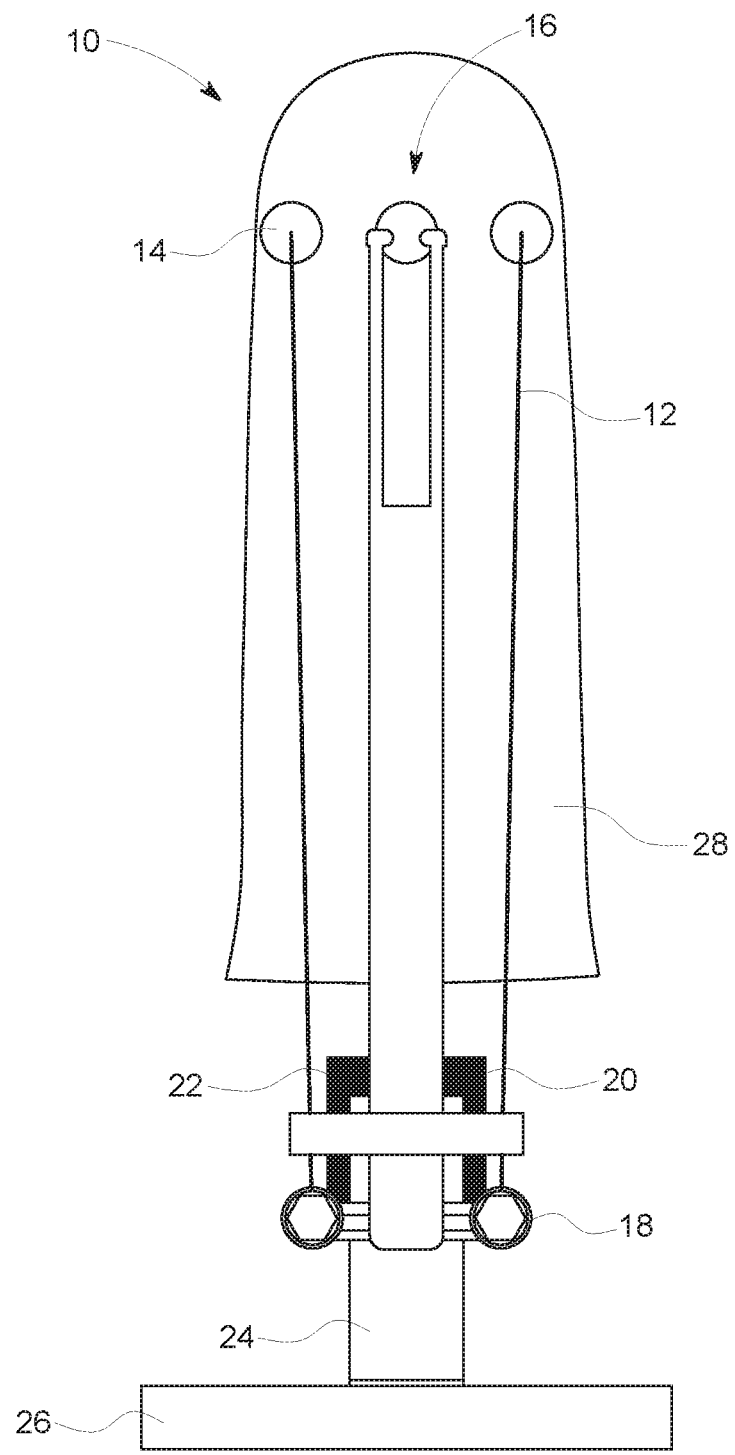
FIG. 1 illustrates a side view of a liner application apparatus, having a liner disposed thereon ready to apply to the user, according to an exemplary embodiment of the present invention.
Figure 2:
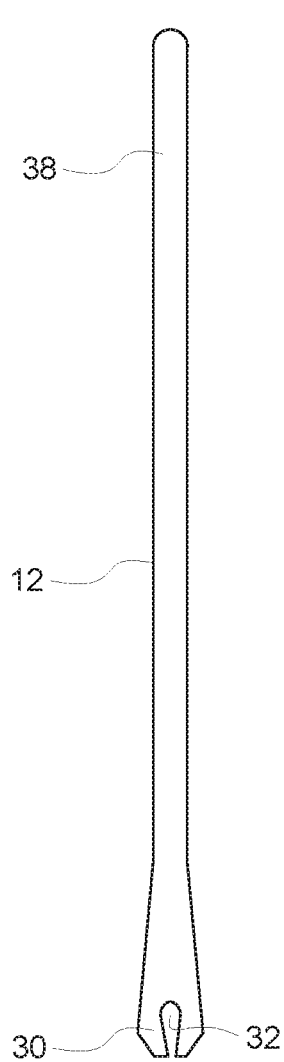
FIG. 2 illustrates a side view of an arm member used in the liner application apparatus of FIG. 1.

Unless otherwise indicated illustrations in the figures are not necessarily drawn to scale.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention and is not intended to limit the invention to the specific embodiments illustrated by the figures or description below.

As is well known to those skilled in the art, many careful considerations and compromises typically must be made when designing for the optimal configuration of a commercial implementation of any device, and in particular, the embodiments of the present invention. A commercial implementation in accordance with the spirit and teachings of the present invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

Broadly, embodiments of the present invention provide an apparatus for use to apply a liner to an appendage of a user includes a base member, a bracket adjustably mounted to the base member to a desired height position, and a plurality of arms pivotably mounted to the bracket. Each arm can include a rotating member, such as a roller ball, coupled to a top end of the arm. The plurality of arms can extend from the bracket in a generally upright position and can support the liner thereon in an inside out position so that the application of downward pressure by the appendage of the user within the plurality of arms permits the arms to pivot outward, thereby allowing the plurality of arms and roller balls to slide the liner around the appendage of the user.

Referring to FIGS. 1 through 8, a liner application device 10, also referred to simply as device 10, can include a base member 26 that may be supported by a surface. The base may include an uprising member, such as extension 24. In some embodiments, the extension 24 may have threads 52 that thread into a central opening 54 in the base member 26. The length of the extension 24 may vary depending on the specific application.

An arm pivot bracket 18, also simply referred to as bracket 18, may be supported by the base member 26. In some embodiments, the bracket 18 may be supported by the extension 24, as shown. The bracket 18 may include a plurality of sides 40 having a cutout to provide a connection location 42 for each of the arms 12, as described below. In some embodiments, the bracket 18 may include one or more set screws 44 that may be used to affix the bracket 18 as a desired height along the extension 24. In other embodiments, the open center 46 of the bracket 18 may include female threads 48 that may engage with threads on the extension 24. In this embodiment, the set screws 44 may not be needed or may be used to restrict inadvertent rotation (and, therefore, inadvertent height adjustment) of the bracket 18 about the extension 24.

Typically, one arm 12 may pivotably attach to and extend upward from each of the connection locations 42 of the bracket 18. From three to ten arms, typically about 6 arms, may extend from the bracket 18. Each arm 12 can include a pivot end 30 with an opening 32 to form the pivoting attachment with the bracket 18. Of course, other pivoting attachment mechanisms may be used within the scope of the present invention, such as a pin, a flexible member, or the like.

Figure 3:
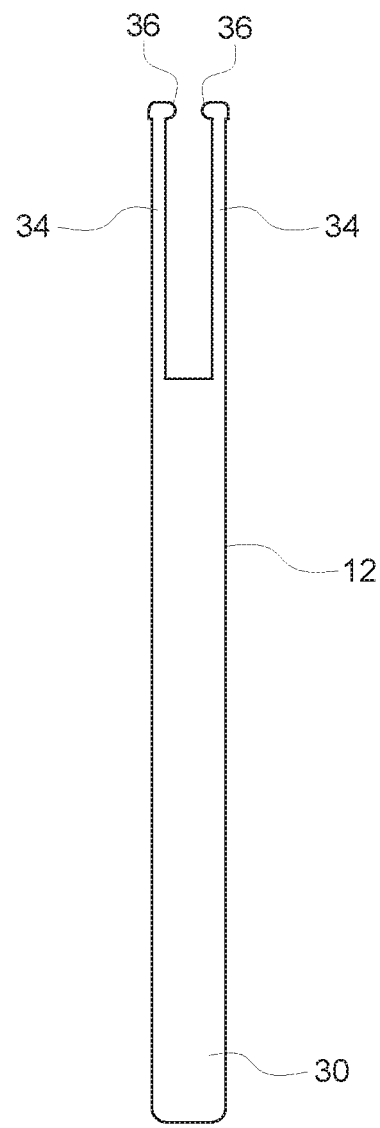
FIG. 3 illustrates a front view of the arm member of FIG. 2.
Figure 4:
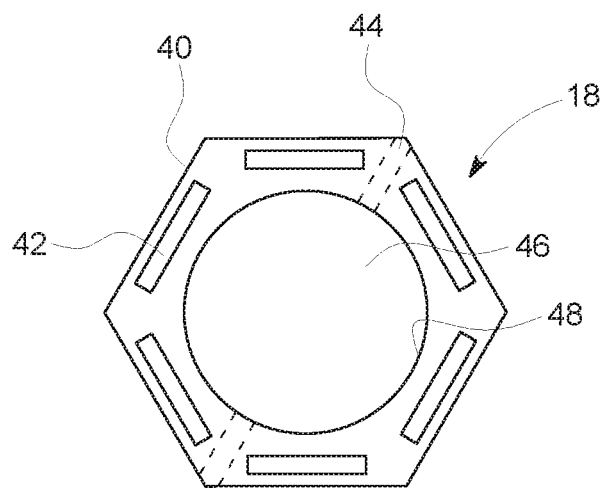
FIG. 4 illustrates a top view of an arm member pivot bracket used in the liner application apparatus of FIGS. 1 and 9.
Figure 5:
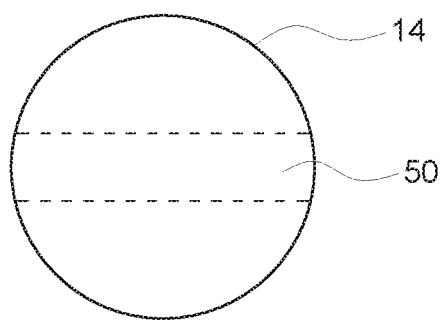
FIG. 5 illustrates a side view of a rotating member used in the liner application apparatus of FIG. 1.
Figure 6:
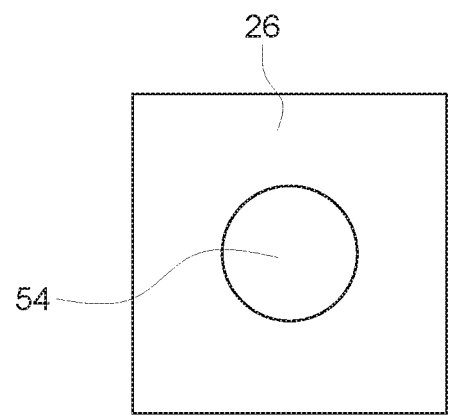
FIG. 6 illustrates a top view of a base member used in the liner application apparatus of FIGS. 1 and 9.
Figure 7:
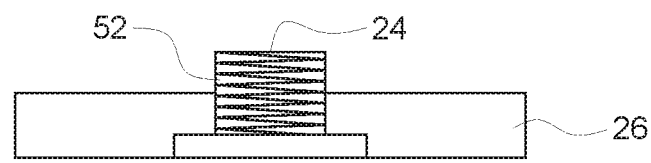
FIG. 7 illustrates a partially cut-away side view of the base member of FIG. 6.
Figure 8:
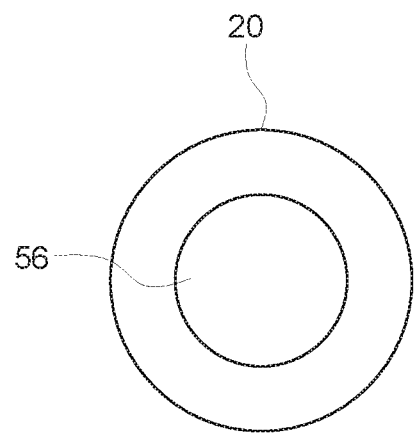
FIG. 8 illustrates a top view of a sleeve used in the liner application apparatus of FIGS. 1 and 9.

A distal end 38 of the arms 12, opposite the pivot end 30, can include a rotating member, such as a rotating ball 14 mounted thereupon. As shown in FIGS. 1, 3 and 5, each arm 12 can include arm extensions 34 with inward facing tabs 36 that can fit into openings 50 in the balls 14, thereby rotationally supporting the balls 14 at the end of each of the arms 12.

A pad 20 may be disposed on and extend upward from the bracket 18, surrounding any portion of the extension 24 that extends above a top portion of the bracket 18. The pad 20 may be an elongated tubular member having an inner opening 56 that may be fit onto the extension 24. The pad 20 may provide a terminus to the inside of the opening 16 so that a user, inserting their appendage into the device 10, does not directly contact the extension 24 at the bottom of the opening 16. Further, the pad 20 can provide a minimal closure of the pivoting arms 12, where a wider pad 20 may form an opening 16 that is wider than that formed with a more narrow pad 20.

Figure 14:
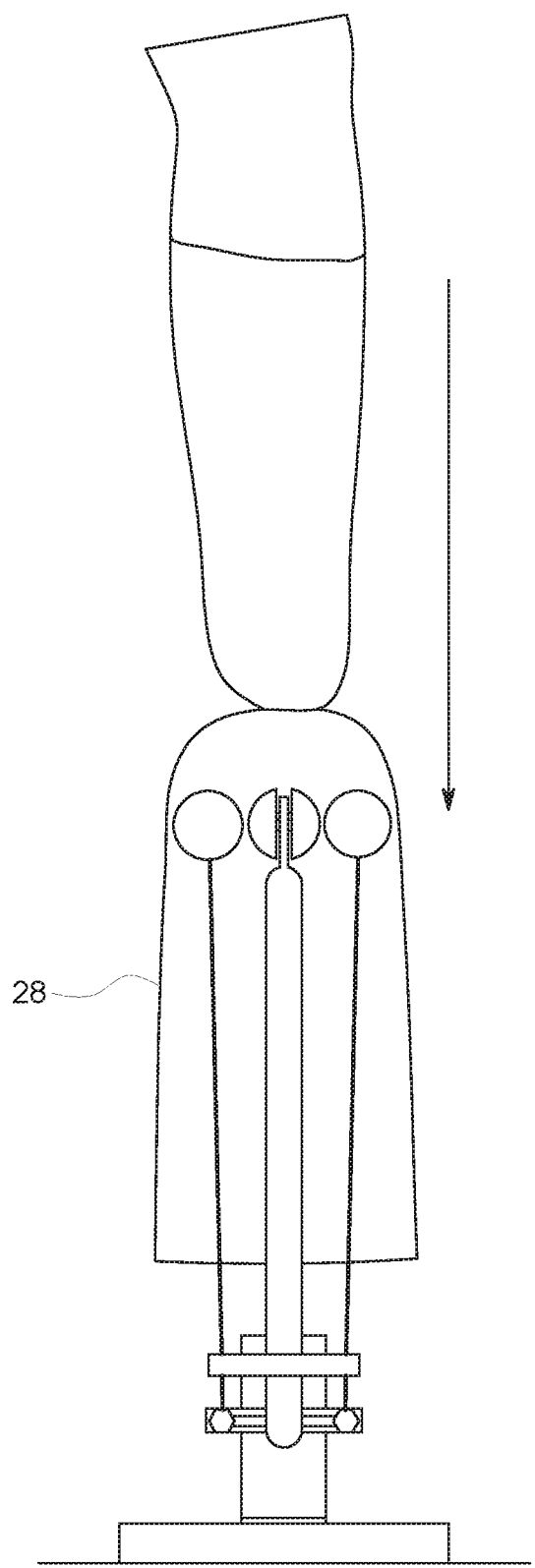
FIG. 14 illustrates a first step to apply a liner to an appendage, where a liner is placed over a liner application apparatus, such as the apparatus of FIGS. 1 and 9.
Figure 15:
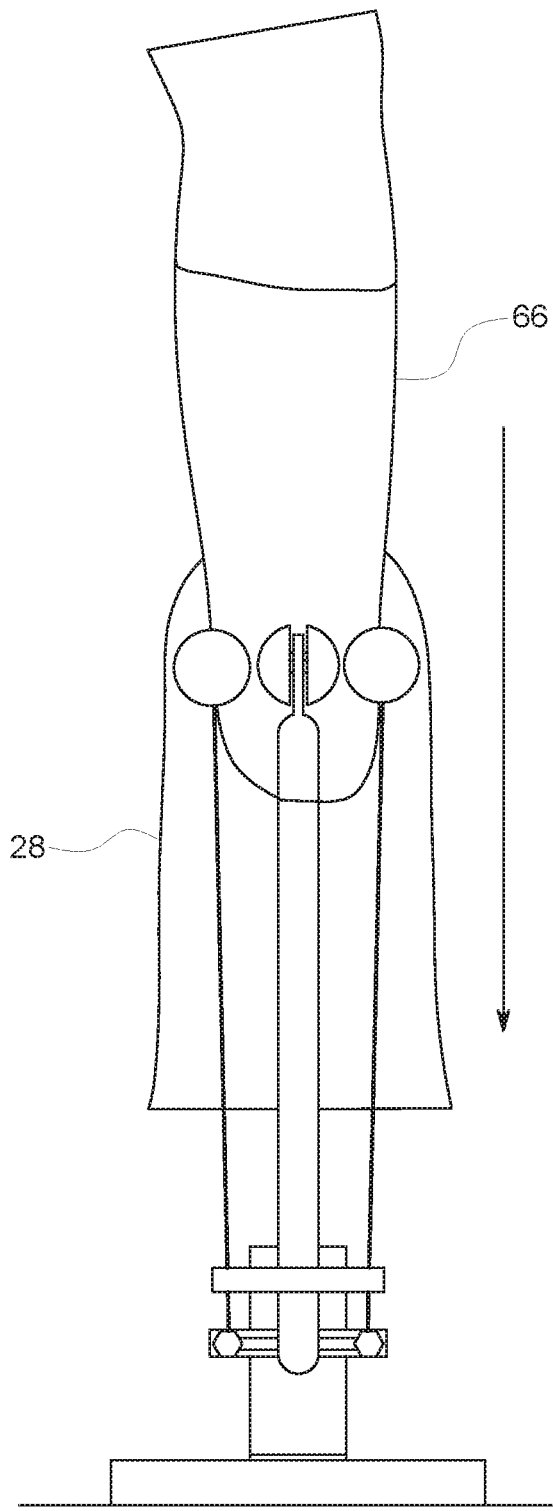
FIG. 15 illustrates a user moving his or her appendage into a space between the rolling elements at the ends of the arms of the liner application apparatus of FIGS. 1 and 9.
Figure 16:
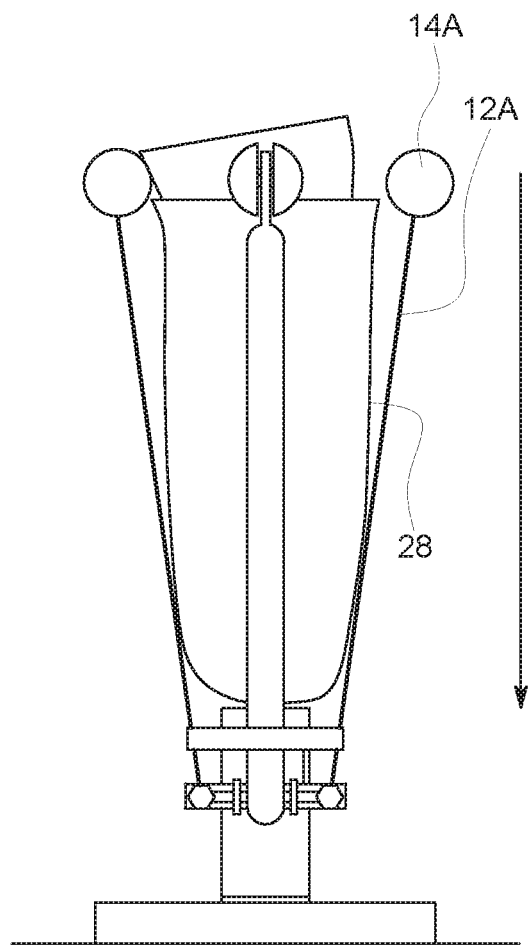
FIG. 16 illustrates the user having his or her appendage fully inserted into the liner application apparatus, thereby completing the application of the liner on the user's appendage.

An elastic member 22 may be disposed about the arms 12 near a pivot end 30 thereof. The elastic member 22 may resiliently hold the arms together, minimizing the size of the opening 16. When the user inserts their appendage 66 into the device 10, as shown in FIGS. 14 through 16, the elastic member 22 an resiliently deform to permit the opening 16 to expand as the user's appendage is moved to a fully inserted position, causing the liner 28, pre-positioned, inside-out, to an exterior of the device 10, to be applied to the appendage in a hands-free manner. While the Figures show the elastic member 22 disposed adjacent the pivot end 30, in some embodiments, the elastic member 22 may be disposed at any position along a length of the arms 12. In some embodiments, an elastic sleeve (not shown) may extend along all or a portion of the arms 12. In any embodiment, the elastic member 22 may be configured to permit the arms to elastically deform outward as the user inserts his or her appendage into the opening 16 of the device 10.

Referring now to FIGS. 9 through 12, in some embodiments, a device 10A can include a ball 14A attached to each arm 12A in an alternate manner. In this embodiment, instead of the arm extensions 34 and tabs 36 fitting into opposite sides of the ball 14 as described above, the ball arms 12A may include a hole 58 at its attachment end 38A, where the ball 14A is formed as two halves, separated by a central connector 62 that extends through the hole 58. This permits the ball 14A to rotate along its central connector 62 in the hole 58.

Figure 12:
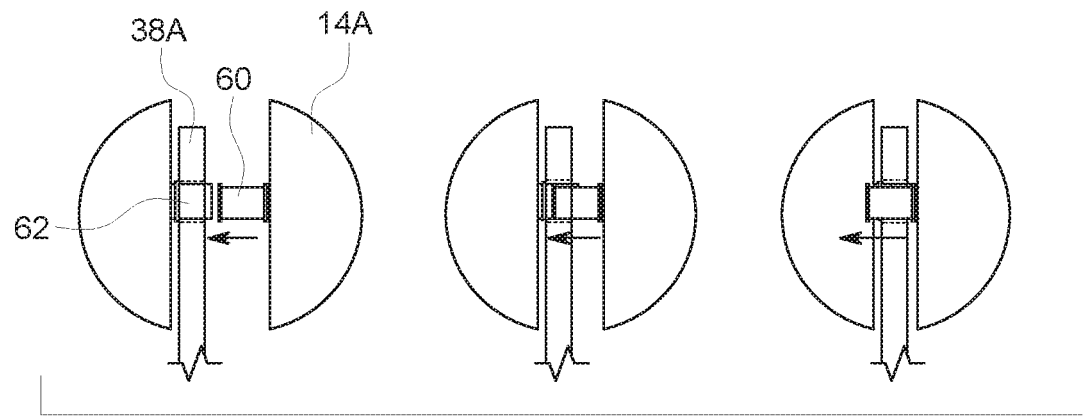
FIG. 12 illustrates an exemplary assembly of the arm and rotating member of FIGS. 10 and 11 that are used with the liner application apparatus of FIG. 9.
Figure 13:
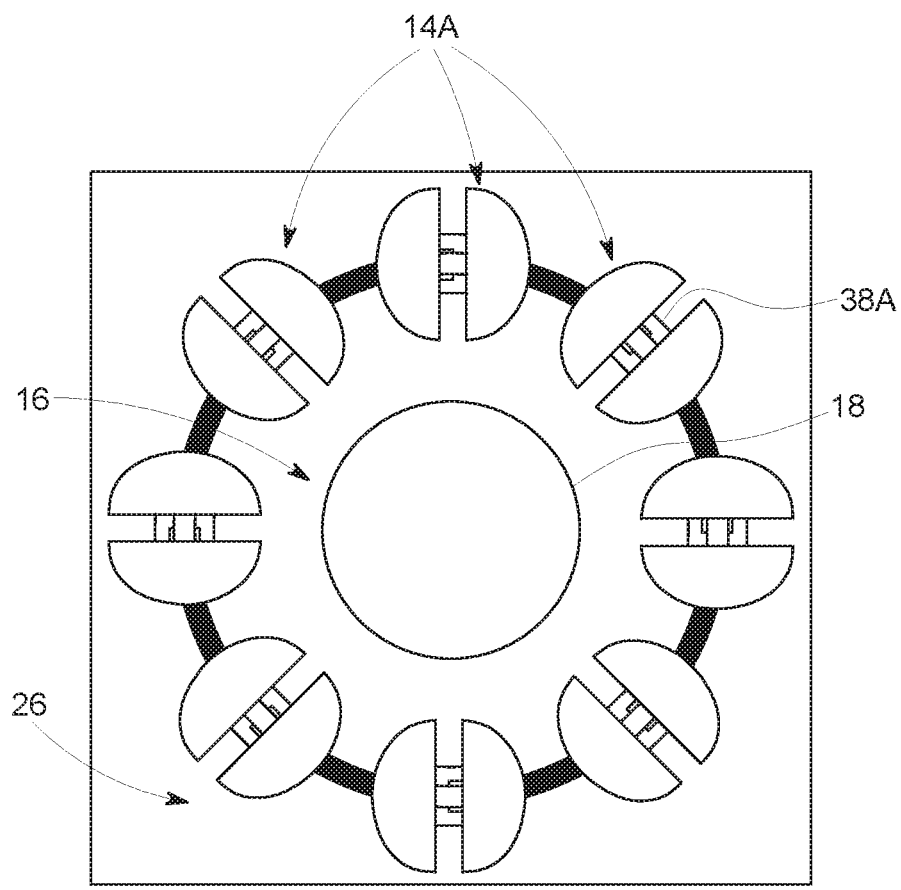
FIG. 13 illustrates a top view of the liner application apparatus of FIG. 9.

In some embodiments, as shown in FIG. 12, the balls 14A may be formed in two halves, one with the central connector 62 and the other with a pin 60 that connects with the central connector 62. Various connection mechanisms may be employed within the scope of the present invention, such as a press fit, a pin and tab, a twist clock, an expended end portion (as shown in FIG. 12), or the like.

Figure 9:
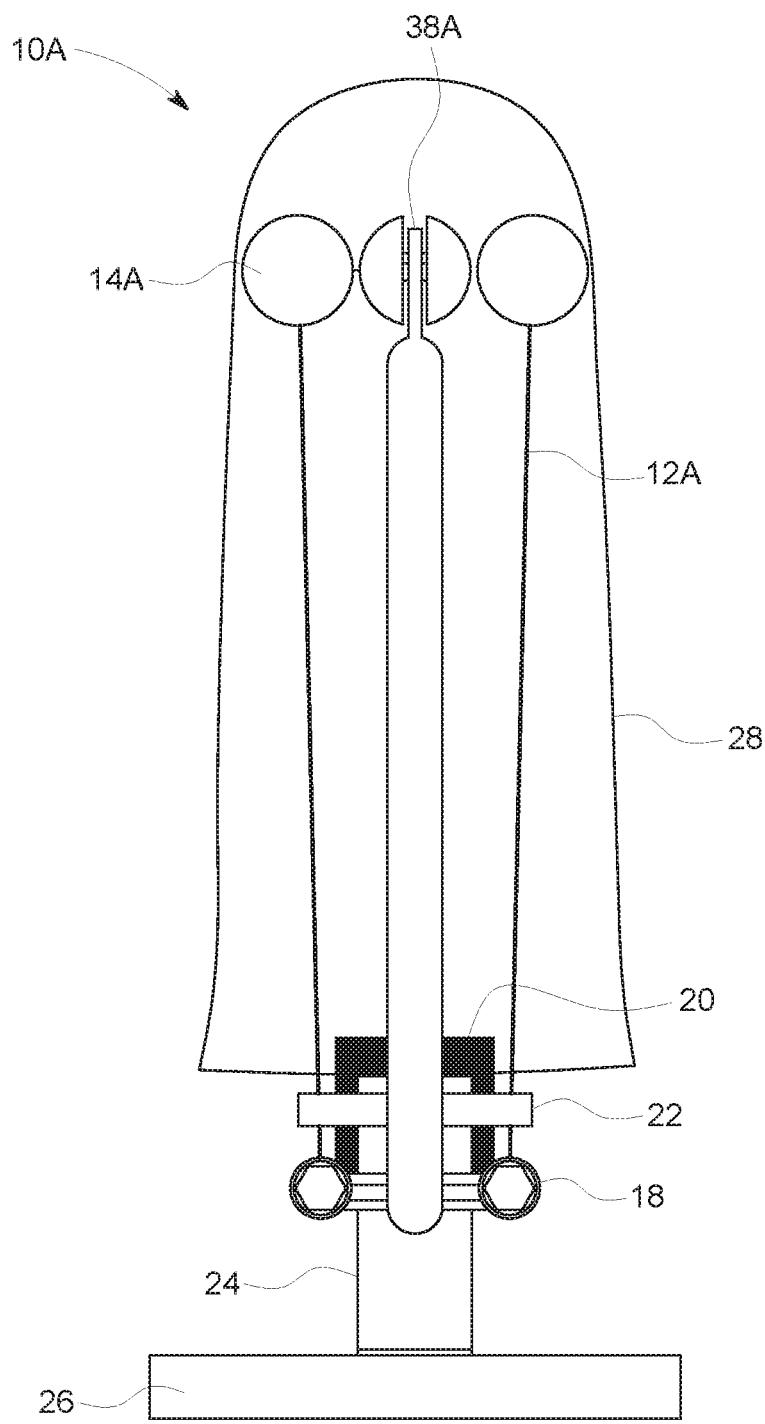
FIG. 9 illustrates a side view of a liner application apparatus, having a liner disposed thereon ready to apply to the user, according to an exemplary embodiment of the present invention.
Figure 10:
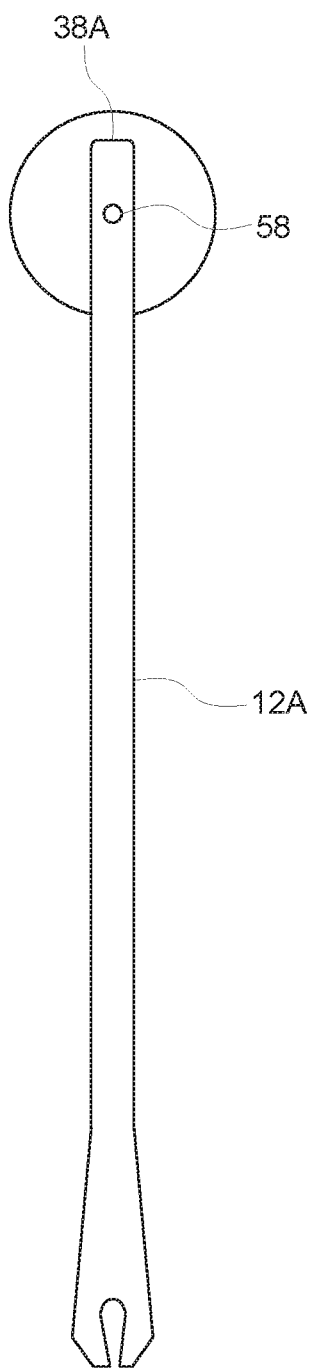
FIG. 10 illustrates a side view of an arm member used in the liner application apparatus of FIG. 9, with the rotating member partially cut-away.
Figure 11:
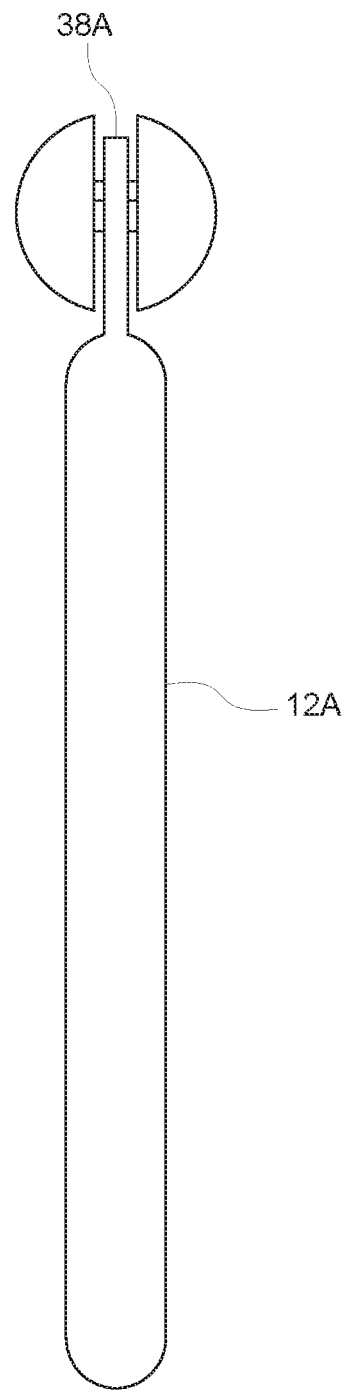
FIG. 11 illustrates a front view of the arm member of FIG. 10.

The operation of the device of FIG. 9 is the same as that of the device of FIG. 1, where the difference is simply in how the balls 14, 14A are mounted to their respective arms 12, 12A. Of course, other ball mount methods may be used within the scope of the present invention. Further, while rotating balls are described above, in some embodiments, the ends of the arms 12, 12A may simply terminate with a rounded element that may not rotate, provided that a user may fit their appendage into the opening 16 formed by the arm ends and further provided that the liner 28 may slide along the ends of the arms as the user fully inserts their appendage into the device to apply the liner 28 thereupon.

The components may be made from conventional materials as known in the art. In some embodiments, the balls 14, 14A may be formed from a material that permits the liner 28 to easily slide therealong, such as nylon, plastic or metal. The arms 12, 12A may be formed from a relatively rigid material, such as plastic, metal or the like. In some embodiments, the components may be 3D-printed. In some embodiments, the arms 12, 12A may be formed from a resiliently flexible material to aid in expanding the opening 16 as the user inserts their appendage. The elastic band 22 may be formed from rubber, fabric, or any similarly resiliently deformable material. The components may be designed to allow the device to be readily assembled or disassembled for ease of transport or storage.

The device 10, 10A may be formed in various sized, depending on the particular user needs. Typically, the opening 16 may be from about 2.5 to about 5 inches, often about 3.5 inches when the arms 12, 12A are in the non-pivoted position, held in place with the elastic band 22. The distance from the opening 16 to the bracket 18 may also vary and may typically be from about 12 to about 30 inches, typically about 18 inches. The base member 26 may have a size sufficient to support the device 10, 10A on a surface. For example, the base member 26 may have dimensions from about 6 to about 12 inches. In some embodiments, the base member 26 may include attachment devices to affix the base member 26 to a surface.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Claim elements and steps herein may have been numbered and/or lettered solely as an aid in readability and understanding. Any such numbering and lettering in itself is not intended to and should not be taken to indicate the ordering of elements and/or steps in the claims.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a sub combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. An apparatus for applying a liner to an appendage of a user, comprising:
   a base member;
   an extension extending from a top side of the base;
   a bracket mounted at the top side of the base member to the extension;
   a pad disposed on and extending upward from a top side of the bracket;
   a plurality of arms, each having a lower end pivotably mounted to the bracket and an upper end having a rotatable ball attached thereto, the plurality of arms extending from the bracket in a generally upright position;
   an opening formed from the upper end of each of the plurality of arms; and
   an elastic band disposed adjacent the lower end of each of the plurality of arms and about an outer side of each of the plurality of arms, the elastic band configured to retain the plurality of arms in the upright position and further permitting the plurality of arms to resiliently move outwardly, causing the opening to expand in size when the user inserts their appendage into the opening,
   wherein the plurality of arms are sized and configured to support a liner thereon in an inside-out position so that the application of downward pressure by the appendage of the user within the plurality of arms permits the arms to pivot outward, thereby allowing the plurality of arms and rotatable balls to slide the liner around the appendage of the user.

2. The apparatus of claim 1, wherein the ball is formed from two separated halves connected by a central connector.

3. The apparatus of claim 2, further comprising a through hole in the upper end of each of the plurality of arms, the through hole receiving the central connector of the ball therein.

4. The apparatus of claim 1, wherein the ball includes a hole in opposite ends thereof, the hole receiving tabs disposed on arm extensions extending from an upper end of each of the plurality of arms.

5. The apparatus of claim 1, wherein the pad is a tubular member.

6. The apparatus of claim 1, wherein each of the plurality of arms are disposed adjacent an outer portion of the pad and pivot away therefrom.

7. The apparatus of claim 1, wherein the bracket has a polygonal shape, where a number of sides of the polygonal shape corresponds to a number of arms in the plurality of arms, wherein one of the plurality of arms is pivotably attached to each side of the polygonal shape.

8. The apparatus of claim 1, wherein the bracket includes one or more set screws for securing a height of the bracket on the extension.

* * * * *